(12) United States Patent
Kjær Thing Riknagel et al.

(10) Patent No.: US 11,617,563 B2
(45) Date of Patent: Apr. 4, 2023

(54) METHOD AND SYSTEM FOR MEASURING A CENTRAL PULSE WAVE VELOCITY IN A PREGNANT WOMAN

(71) Applicant: VIEWCARE TECHNOLOGIES 1 APS, Søborg (DK)

(72) Inventors: Diana Kjær Thing Riknagel, Gedsted (DK); Johannes Jan Struijk, Terndrup (DK)

(73) Assignee: VIEWCARE TECHNOLOGIES 1 APS, Søborg (DK)

( * ) Notice: Subject to any disclaimer, the term of this patent is extended or adjusted under 35 U.S.C. 154(b) by 1153 days.

(21) Appl. No.: 16/307,721

(22) PCT Filed: Jun. 7, 2017

(86) PCT No.: PCT/EP2017/063784
§ 371 (c)(1),
(2) Date: Dec. 6, 2018

(87) PCT Pub. No.: WO2017/211869
PCT Pub. Date: Dec. 14, 2017

(65) Prior Publication Data
US 2019/0183454 A1    Jun. 20, 2019

(30) Foreign Application Priority Data
Jun. 7, 2016 (SE) .................................... 1650791-5

(51) Int. Cl.
*A61B 8/08* (2006.01)
*A61B 5/00* (2006.01)
(Continued)

(52) U.S. Cl.
CPC ........ *A61B 8/0866* (2013.01); *A61B 5/02007* (2013.01); *A61B 5/4343* (2013.01);
(Continued)

(58) Field of Classification Search
CPC ....... A61B 8/02; A61B 8/4477; A61B 8/5223; A61B 5/02007; A61B 8/0866;
(Continued)

(56) References Cited

U.S. PATENT DOCUMENTS

| | | | |
|---|---|---|---|
| 2009/0187110 A1 | 7/2009 | Voss et al. | |
| 2012/0179053 A1* | 7/2012 | Gemignani | A61B 5/02133 600/485 |

(Continued)

FOREIGN PATENT DOCUMENTS

| | | |
|---|---|---|
| CN | 103139438 A | 6/2013 |
| CN | 203182903 U | 9/2013 |

(Continued)

OTHER PUBLICATIONS

International Search Report dated Oct. 17, 2017, issued in corresponding International Application No. PCT/EP2017/063784, filed Jun. 7, 2017, 3 pages.

(Continued)

*Primary Examiner* — Brenda C Bernardi
(74) *Attorney, Agent, or Firm* — Christensen O'Connor Johnson Kindness PLLC (57) ABSTRACT

The present invention relates to a method and system for determining a central pulse wave velocity in a pregnant woman. The method comprises receiving an indication of a measurement of a length of a human aortic path outside the body to provide an aortic length, arranging a sound transducer at the position of the anatomical projection of the uterine artery, identifying the opening of the maternal aortic valve with measurement from the sound transducer as a first time, and the pulse wave arrival time at the uterine artery with measurements from the sound transducer as a second time, determining the central transit time based on the difference between the second time and the first time, and (Continued)

calculating the central pulse wave velocity based on the aortic length and the central transit time.

16 Claims, 4 Drawing Sheets

(51) Int. Cl.
*A61B 5/02* (2006.01)
*A61B 7/02* (2006.01)
*A61B 7/04* (2006.01)
*A61B 8/02* (2006.01)
*A61B 8/00* (2006.01)
*A61B 5/107* (2006.01)
*A61B 5/021* (2006.01)

(52) U.S. Cl.
CPC .............. *A61B 7/026* (2013.01); *A61B 7/04* (2013.01); *A61B 8/02* (2013.01); *A61B 8/0891* (2013.01); *A61B 8/4477* (2013.01); *A61B 8/461* (2013.01); *A61B 8/467* (2013.01); *A61B 8/5223* (2013.01); *A61B 8/54* (2013.01); *A61B 5/02125* (2013.01); *A61B 5/1072* (2013.01)

(58) Field of Classification Search
CPC .. A61B 7/026; A61B 7/00; A61B 7/04; A61B 5/4343; A61B 8/54; A61B 8/461; A61B 8/0891; A61B 8/467; A61B 5/1072; A61B 5/02125

See application file for complete search history.

(56) References Cited

U.S. PATENT DOCUMENTS

2013/0194298 A1* 8/2013 Takabatake ............ G06V 10/44
345/629
2015/0018635 A1* 1/2015 Dinesen ................. A61B 5/389
600/301
2015/0164404 A1 6/2015 Euliano et al.
2016/0073911 A1 3/2016 Hallab
2017/0258436 A1* 9/2017 Kjær Thing Riknagel .................
A61B 7/00

FOREIGN PATENT DOCUMENTS

| CN | 104053401 A | 9/2014 |
|---|---|---|
| EP | 1 230 897 A1 | 8/2002 |
| WO | 03/088841 A2 | 10/2003 |
| WO | 2009/125349 A2 | 10/2009 |
| WO | 2011/039580 A2 | 4/2011 |
| WO | 2011/120973 A1 | 10/2011 |
| WO | 2013/079073 A1 | 6/2013 |
| WO | 2016/059206 A1 | 4/2016 |

OTHER PUBLICATIONS

Swedish Office Action dated Jan. 16, 2017, issued in corresponding Swedish Application No. 1650791-5, filed Jun. 7, 2016, 8 pages.
Khalil, A., et al., "O113. Measurements of Arterial Stiffness and Uterine Artery Doppler for the Prediction of Preeclampsia in Women Presenting With Gestational Hypertension," Pregnancy Hyptertension 5(3):233-234, Jul. 2015.
Miyashita, S., et al., "Evaluation of Pulse Wave Velocity and Pulse Pressure Using Ultrasonic Phased-Tracking Method in Normal and Growth-Restricted Fetuses," Ultrasound in Obstetrics & Gynecology 44(Suppl. 1):1-61, 2014; Proceedings of the 24th World Congress on Ultrasound in Obstetrics and Gynecology, Barcelona, Sep. 14-17, 2014.
Nye, E.R., "The Effect of Blood Pressure Alteration on the Pulse Wave Velocity," British Heart Journal 26(2):261-265, Mar. 1964.

* cited by examiner

METHOD AND SYSTEM FOR MEASURING A CENTRAL PULSE WAVE VELOCITY IN A PREGNANT WOMAN

TECHNICAL FIELD

The present invention relates to a method for determining the central pulse wave velocity in a pregnant woman, and a system for determining the central pulse wave velocity in a pregnant woman.

BACKGROUND ART

Arterial Pulse Wave Velocity (APWV) is the velocity with which the heartbeat-initiated pressure pulse travels along an artery. The clinical importance of Arterial PWV is derived from its correlation with vessel wall stiffness, which is the elasticity (compliance) of the arteries, describing the capability of an artery to expand and to contract in response to pressure changes. Arterial PWV is thus a valuable measure of peripheral arterial condition and is widely accepted as the "gold standard" measure of arterial stiffness.

In recent years a number of attempts have been made to identify markers of both local and systemic changes related to pregnancy induced hypertension (PIH) and especially pre-eclampsia (PE). The increased understanding of the causal pathophysiology has led to attempts to predict the disease before onset of clinical manifestations, including screening methods of the vascular alterations by uterine artery Doppler velocimetry, placental perfusion by magnetic resonance imaging and, recently, by applying vascular measures, such as the carotid-femoral pulse wave velocity (cfPWV). The latter method is, besides being a predictor of cardiovascular disease in the general population, a measure of the aortic stiffness in pregnancy, which is associated with pre-eclampsia.

However, a central Pulse Wave Velocity (cPWV), defining a velocity of the pulse wave from the aortic valve to the uterine artery, is even more interesting, since it is directly related to the stiffness of the aorta and larger arteries.

Hence, there is a desire to provide a method and system which can provide an accurate non-invasive measurement of the average cPWV with a relatively low cost and complexity.

SUMMARY OF THE INVENTION

It is an object of the present invention to improve the current state of the art, to at least partly solve the above problems, and to provide a non-invasive measurement of the central Pulse Wave Velocity (cPWV) in pregnant women. These and other objects are achieved by a method for determining a central pulse wave velocity in a pregnant woman, and a system for determining a central pulse wave velocity in a pregnant woman.

According to a first aspect of the present invention, a method for determining a central pulse wave velocity in a pregnant woman is provided. The method comprises:
  receiving an indication of a measurement of a length of a human aortic path outside the body to provide an aortic length;
  arranging a sound transducer, outside the body of the patient, at the position of the anatomical projection of the uterine artery;
  identifying the opening of the maternal aortic valve with measurement from the sound transducer as a first time, and the pulse wave arrival time at the uterine artery with measurements from the sound transducer as a second time;
  determining the central transit time based on the difference between the second time and the first time; and
  calculating the central pulse wave velocity based on the aortic length and the central transit time.

According to at least a second aspect of the present invention, a system for determining a central pulse wave velocity in a pregnant woman is provided. The system comprises:
  a sound transducer adapted to measure the opening of the maternal aortic valve and the pulse wave arrival time at the uterine artery with measurements;
  a control unit connected to the sound transducer; and
  wherein the control unit is configured to receive measurement signals from the sound transducer to identify the opening of the maternal aortic valve as a first time, and to receive measurements signals from the sound transducer to identify the pulse wave arrival time at the uterine artery as a second time, and wherein the control unit is further configured to determine the central transit time based on the difference between the second time and the first time and calculate the central pulse wave velocity based on an aortic path length measurement and the central transit time.

The present invention is based on the realization that a precise non-invasive measure of a central pulse wave velocity (cPWV) may be provided by a single sound transducer arranged outside the body of the patient. The sound transducer is used to measure different characteristics of sounds originating from the body. It is typically not possible to measure the opening of the aortic valve from the lower abdomen and arteries, such as the uterine artery or the femoral artery. However, it is an insight of the invention that in pregnant women the presence of the fluid-filled enlarged uterus conducts the maternal heart sound to the abdomen. This enables the single sound transducer to measure the opening of the maternal aortic valve and also the arrival of the pulse wave in the uterine artery. On the basis of the sounds thus recorded, it is possible to calculate the central pulse wave velocity. Hence, the present invention enables a convenient, simple and cost-effective measurement of the cPWV. Further, the system is easy and quick to handle and little expertise is needed to operate the system.

As noted in the foregoing, an abnormal cPWV may be indicative of various problematic conditions such as hypertension and pre-eclampsia. The cfPWV is increased in pre-eclamptic women compared to normotensive women both during and after pregnancy. Also, the increase in cfPWV is greater in more severe forms of pre-eclampsia and in early-onset pre-eclampsia. Hence, the cPWV measurement is an intermediate finding which has diagnostic relevance and may prompt further tests on the patient to determine the cause of an abnormal cPWV.

In at least one exemplary embodiment, the method is repeated to provide an average central pulse wave velocity from a plurality of measurements by the sound transducer. In at least one exemplary embodiment, the control unit is configured to calculate an average central pulse wave velocity from a plurality of measurements by the sound transducer. By using a plurality of measurements, the reliability of calculated average aortic pulse wave velocity may be more robust.

The length of the human aorta may be approximated as the distance from the position of the hyoid bone to the position to the umbilicus. In the present invention, the length of the common and internal iliac arteries down to the uterine artery may also be needed to define the length of a human aortic path, as sound corresponding to a pulse wave reaching the uterine artery is obtained. Therefore, the total length travelled by blood flow from the aortic valve to the uterine artery may be provided as the length of a human aortic path, e.g. measured or indicated as the position of the hyoid bone to the position of the anatomical projection of the uterine artery. It should be realized, however, that other measurements may be performed to approximate the length of travel of blood flow. For example, a measurement of the aortic length from the position of the hyoid bone to the position of the umbilicus may be used and multiplied with a factor for obtaining a measurement of the length of the aortic path relevant to the travel of blood flow. Further, the patient records may contain prior measurements or approximations of the aortic length made by MRI, X-ray or the like. From the foregoing is should be understood that the aortic path length should be interpreted as the approximated or measured length of the aortic path from the beginning of the aorta, i.e. the aortic valve, to the start of the uterine artery, i.e. the bifurcation from the iliac arteries which open into the uterine artery.

The anatomical projection of the uterine artery should be understood as the anatomical projection on the front side of the body of the patient.

The sound transducer is arranged at the anatomical projection of the uterine artery for measuring aortic valve opening time. The term at the anatomical projection of the uterine artery should of course be interpreted as in the vicinity of the anatomical projection of the uterine artery. For example, it may be sufficient to arrange the sound transducer within a 10 cm radius from the anatomical projection of the uterine artery. The sound transducer may be releasably fastened to a patient utilizing an adhesive, or an adhesive tape. The sound transducer may alternatively be known as microphones. As an alternative, the sound transducer may be an accelerometer, which is able to convert vibrations caused by the sounds from the maternal aortic valve opening and pulse wave arrival, respectively, to a recorded signal.

In at least one exemplary embodiment, the sound transducer is a first sound transducer and the method further comprises arranging a second sound transducer, outside the body of the patient, contralateral on the abdomen to the position of the first sound transducer. The second sound transducer may be used to augment or replace the measured signal from the first sound transducer. This is due to the fact that some sounds may be stronger on one or the other side of the body of the patient.

In at least one exemplary embodiment, the sound transducer is a first sound transducer and the system further comprises a second sound transducer adapted to measure the opening of the maternal aortic valve and the pulse wave arrival time at the uterine artery with measurements, wherein the second sound transducer is adapted to be placed contralateral on the abdomen to the position of the first sound transducer and augment or replace the measurements of the first sound transducer.

Measurements by the second sound transducer may for instance augment measurements by the first sound transducer by a mean cPWV value being formed based on measurements from both the first and the second sound transducers.

In at least one exemplary embodiment, the sound transducer is a first sound transducer and the system further comprises a third sound transducer adapted to measure the opening of the maternal aortic valve, wherein the third sound transducer is adapted to be placed at the aortic valve auscultation region of the patient for measuring the maternal aortic valve opening time and replace the measurements of the first sound transducer with respect to identifying the maternal valve opening time.

Hence, identifying the opening of the maternal aortic valve is instead accomplished with measurement from the third sound transducer as a first time, and identifying the pulse wave arrival time at the uterine artery is still accomplished with measurements from the first sound transducer as a second time. It should of course be noted that the third sound transducer may be the only one of two sound transducers used, and the term third is only used for the sake of convenience and differentiation between the second sound transducer and the third sound transducer.

In at least one exemplary embodiment, the sound transducer is a first sound transducer and the system further comprises a second sound transducer adapted to measure the opening of the maternal aortic valve and the pulse wave arrival time at the uterine artery with measurements, wherein the second sound transducer is adapted to be placed contralateral on the abdomen to the position of the first sound transducer and augment or replace the measurements of the first sound transducer, and wherein the system further comprises a third sound transducer adapted to measure the opening of the maternal aortic valve, wherein the third sound transducer is adapted to be placed at the aortic valve auscultation region of the patient for measuring the maternal aortic valve opening time and replace the measurements of the first sound transducer with respect to identifying the maternal valve opening time.

Hence, identifying the opening of the maternal aortic valve is instead accomplished with measurement from the third sound transducer as a first time, and identifying the pulse wave arrival time at the uterine artery is still accomplished with measurements from the first sound transducer as a second time. The second sound transducer is used to augment or replace the measurements of the first sound transducer to identify the opening of the maternal aortic valve as a second time.

According to another exemplary embodiment, an electrode pair, such as an electrocardiogram (ECG) electrode pair is used for identifying the opening of the maternal aortic valve. The maternal ECG can be related to the timing of when the aortic valve is opening and can thus be used for determining the opening of the maternal aortic valve as a first time. For instance, an R-wave may be detected from the maternal ECG and may be related to the opening of the maternal aortic valve. The ECG electrode pair may be arranged on the maternal chest or maternal abdomen, and exact placement of the ECG electrode is not very critical, since the R-wave may be detected from almost any position on the abdomen or chest.

The electrode pair may form a single lead for detecting the ECG. However, several electrodes forming multiple leads may alternatively be used.

The ECG electrodes may be arranged in the same housing, being encapsulated with the first sound transducer. However, the ECG electrodes may alternatively be separately arranged on the maternal abdomen or chest.

According to an exemplary embodiment, a method for determining a central pulse wave velocity in a pregnant woman is provided. The method comprises: receiving an indication of a measurement of a length of a human aortic path outside the body to provide an aortic length; arranging a sound transducer, outside the body of the patient, at the position of the anatomical projection of the uterine artery;

arranging an ECG electrode pair, outside the body of the patient, to detect maternal heart activity; identifying the opening of the maternal aortic valve with measurement from the ECG electrode pair as a first time, and identifying the pulse wave arrival time at the uterine artery with measurements from the sound transducer as a second time; determining the central transit time based on the difference between the second time and the first time; and calculating the central pulse wave velocity based on the aortic length and the central transit time.

The first, second and third sound transducers and ECG electrodes may be synchronized. The first, second and third sound transducers and ECG electrodes may be synchronized by any known means, for example the measurement from the first, second and third sound transducers may be time-stamped. Alternatively, analog-to-digital converter(s) for converting the signals from the first, second, and third sound transducers and the ECG electrodes may use the same clock. As a further alternative, the control unit connected to both the first, second and third sound transducer and ECG electrodes may synchronize the received measurement signals.

The sound transducer(s) and ECG electrodes may be wired or wirelessly connected to the control unit. Alternatively, a sound transducer may be connected to another sound transducer, which in turn may be connected to the control unit such that a signal from one sound transducer may be transmitted to another sound transducer, whereas signals from several sound transducers may be transmitted (in separate channels) from the same sound transducer to the control unit. The sound transducer(s) may be wirelessly connected via a Bluetooth piconet or through other wireless protocols and standards such as WiFi. Thus making handling the system very easy and quick and with little expertise needed.

In at least one exemplary embodiment, the opening of the maternal aortic valve is identified by means of the first sound transducer by sounds having a frequency range below 100 Hz. In at least one exemplary embodiment, the opening of the maternal aortic valve is identified by sounds having a frequency range below 200 Hz. In at least one exemplary embodiment, the opening of the maternal aortic valve is identified by sounds having a frequency range below 50 Hz. The opening of the aortic valve is preferably identified by the S1-heart sound. The S1-heart sound typically comprises sound in the frequencies of 25 Hz to 200 Hz. Therefore the identification of the low frequency heart sound may be facilitated in a frequency range below 200 Hz, and preferably in a range of 25-200 Hz.

In at least one exemplary embodiment, the opening of the aortic valve is identified by means of the third sound transducer by sounds having a frequency in the range of 25 Hz to 300 Hz. In at least one exemplary embodiment, the opening of the aortic valve is identified by sounds having a frequency in the range of 1 Hz to 300 Hz. In at least one exemplary embodiment, the opening of the aortic valve is identified by sounds having a frequency in the range of 25 Hz to 200 Hz. In at least one exemplary embodiment, the opening of the aortic valve is identified by sounds having a frequency in the range of 1 Hz to 25 Hz. The opening of the aortic valve is preferably identified by a low frequency heart sound which occurs simultaneously as the S1-heart sound. The low frequency heart sound comprises sounds waves in the frequency range of 1 Hz to 25 Hz. Therefore the identification of the low frequency heart sound may be facilitated in the frequency range of 1 Hz to 25 Hz. However, using a larger frequency range may also provide more information, such that the low frequency heart sound may be more easily distinguished from the S1 heart sound.

In at least one exemplary embodiment, the pulse wave arrival time at the uterine artery is identified by sounds having a frequency range of 200 Hz to 800 Hz. Stated differently, the pulse wave arrival time at the uterine artery is identified by the murmur caused by the interaction of the pulse wave with the uterine artery.

In at least one exemplary embodiment, identifying the opening of the maternal aortic valve with measurement from the sound transducer as a first time, and the pulse wave arrival time at the uterine artery with measurements from the sound transducer as a second time is performed automatically by a control unit comprising a processor. The opening of the maternal aortic valve and the pulse wave arrival time at the uterine artery may be identified with a computer based interpretation of the signals.

For example, a database which comprises a large number of validation measurements of the sounds signals in healthy subjects may be used. Then, the processor may use curve fitting, least squares approximation, or machine learning to identify the opening of the maternal aortic valve and the pulse wave arrival time at the uterine artery as measurement signals from the sound transducer which are similar and comparable to the measurement from healthy subjects.

As an alternative, an algorithm for processing the received signal may be used, wherein the algorithm is adapted to detect and identify the points in time.

In at least one exemplary embodiment, the system further comprises a display and user input means. The display may be any known display in the art such as an LCD, LED or OLED display. The user input means may be any known user input means in the art such as a touch-interface, e.g. on the display, a keypad, a keyboard, a mouse or other pointer input means.

In at least one exemplary embodiment, the method further comprises:
  displaying the measurements from the sound transducer on a display;
  receiving user input to identify the first time and the second time; and
  correcting the first time and the second time based on the user input, wherein the corrected first and second time are used for determining the central transit time and calculating the central pulse wave velocity.

In at least one exemplary embodiment, the control unit is configured to display the measurements from the sound transducer on the display, and to receive user input to identify the first time and the second time, wherein the control unit is configured to correct the first time and the second time based on the user input, wherein the corrected first and second time are used to determine the central transit time and calculate the central pulse wave velocity.

Stated differently, a user may provide input such that the first and second time is corrected or verified. Human beings have an enormous potential for finding patterns, and it may be useful to verify or correct the identification of the first time and the second time. The user input may advantageously be used to further teach the control unit, e.g. using machine learning, by adding the correct first time and second time to a database.

In at least one exemplary embodiment, identifying the opening of the maternal aortic valve with measurement from the sound transducer as a first time, and the pulse wave arrival time at the uterine artery with measurements from the sound transducer as a second time further comprises:

displaying the measurements from the sound transducer on a display;

receiving user input to identify the first time and the second time.

Stated differently, the measurements are presented to a user on a display and the user provides input to identify the opening of the maternal aortic valve and the pulse wave arrival time at the uterine artery as the first and second time.

According to at least a third aspect of the present invention, a system for determining an average central pulse wave velocity in a pregnant woman is provided. The system comprises:

a sound transducer adapted to measure the opening of the maternal aortic valve and the pulse wave arrival time at the uterine artery;

a display;

user input means;

a control unit connected to the sound transducer, the display and the user input means; and wherein the control unit is configured to receive measurement signals from the sound transducer, and display the measurements on the display, and to receive user input via the user input means to identify the opening of the maternal aortic valve as a first time and the pulse wave arrival time at the uterine artery as a second time, and to receive an aortic length measurement, wherein the control unit is further configured to determine the central transit time based on the difference between the second time and the first time and calculate the central pulse wave velocity based on an aortic length measurement and the central transit time.

Effects and features of this third aspect of the present invention are largely analogous to those described above in connection with the first and second aspect of the inventive concept. Embodiments mentioned in relation to the first and second aspect of the present invention are largely compatible with the third aspect of the invention.

According to at least a third aspect of the present invention, a method for determining a central pulse wave velocity in a pregnant woman is provided. The method comprises:

receiving an indication of a measurement of a length of a human aortic path outside the body to provide an aortic length;

arranging a first sound transducer outside the body of the patient for measuring the opening of the maternal aortic valve;

arranging a second sound transducer outside the body of the patient for measuring the pulse wave arrival time at the uterine artery;

identifying the opening of the aortic valve with measurement from the first sound transducer as a first time, and the pulse wave arrival time at the uterine artery with measurements from the second sound transducer as a second time;

determining the central transit time based on the difference between the second time and the first time; and calculating the central pulse wave velocity based on the length of the human aortic path and the central transit time.

According to at least a fifth aspect of the present invention, a system for determining a central pulse wave velocity in a pregnant woman is provided. The system comprises:

a first sound transducer adapted to measure the opening of the maternal aortic valve;

a second sound transducer adapted to measure the pulse wave arrival time at the uterine artery;

a control unit connected to the first sound transducer and to the second sound transducer; and wherein the control unit is configured to receive measurement signals from the first sound transducer to identify the opening of the maternal aortic valve as a first time, and to receive measurements signals from the second sound transducer to identify the pulse wave arrival time at the uterine artery as a second time, and wherein the control unit is further configured to determine the central transit time based on the difference between the second time and the first time and calculate the central pulse wave velocity based on an aortic path length measurement and the central transit time.

According to the fourth and fifth aspects of the invention, a first sound transducer (corresponding to the third sound transducer discussed above with respect to the first to third aspects of the invention) is used for determining the opening of the maternal aortic valve. The second sound transducer (corresponding to the first (or second) sound transducer discussed above with respect to the first to third aspects of the invention) is used for determining the pulse wave arrival time at the uterine artery. Thus, the central pulse wave velocity may be determined based on these two sound transducers obtaining measurements of the opening of the maternal aortic valve and the pulse wave arrival time at the uterine artery, respectively. The second sound transducer arranged at the uterine artery need not necessarily measure the opening of the maternal aortic valve, at all.

Apart from the above, effects and features of these fourth and fifth aspects of the present invention are largely analogous to those described above in connection with the first, second, and third aspects of the inventive concept. Embodiments mentioned in relation to the first, second and third aspects of the present invention are largely compatible with the fourth and fifth aspects of the invention.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of the element, device, component, means, step, etc., unless explicitly stated otherwise.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

DETAILED DESCRIPTION OF PREFERRED EMBODIMENTS OF THE INVENTION

In the present detailed description, embodiments of a method and system are discussed. It should be noted that this by no means limits the scope of the invention, which is also applicable in other circumstances for instance with other types or variants of systems than the ones shown in the appended drawings. Further, that specific components are mentioned in connection to an embodiment of the invention does not mean that those components cannot be used to an advantage together with other embodiments of the invention.

The present invention encompasses methods and system for determining a central pulse wave velocity in a pregnant woman by way of recorded signals from a sound transducer. An abnormal central pulse wave velocity may indicate both local and systemic changes related to pregnancy induced hypertension (PIH) and pre-eclampsia (PE), and is thus a finding of intermediate diagnostic relevance which may prompt further examinations of the patient in question.

Figure 1:
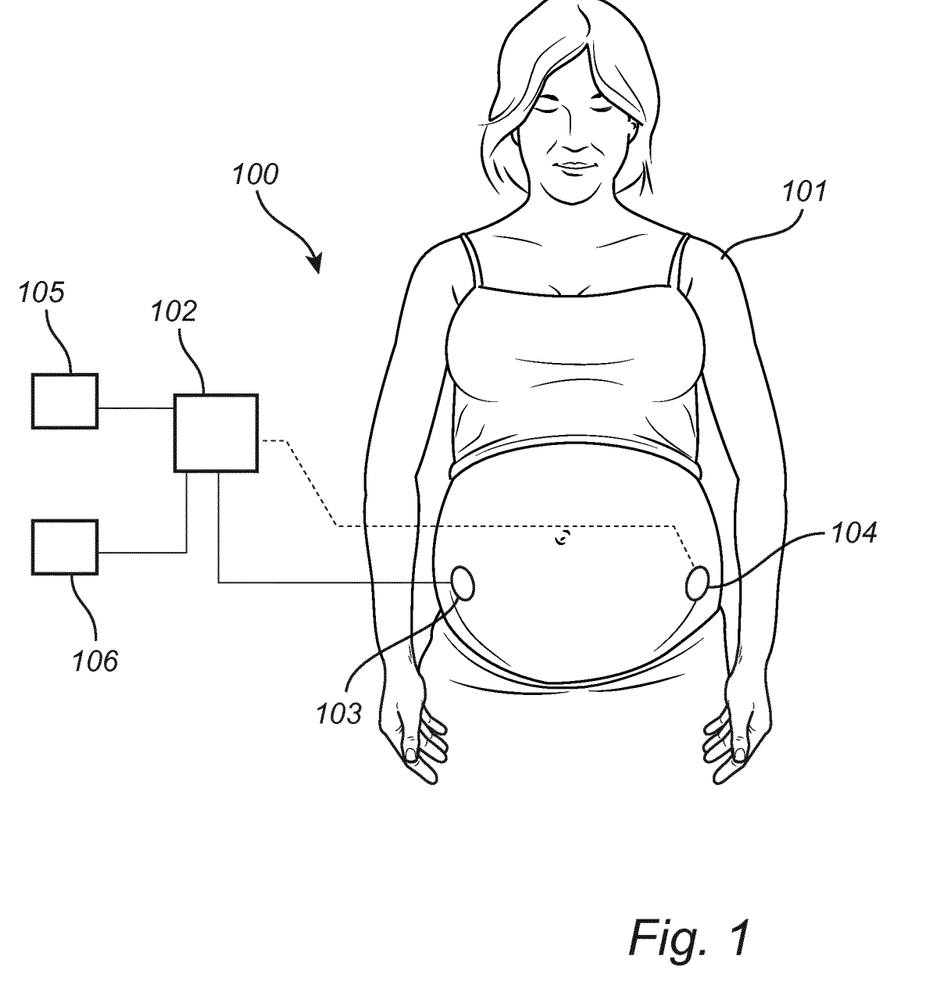
FIG. 1 is schematic view of a system according to at least one example embodiment of the invention.

FIG. 1 is a schematic view of a system 100 for determining the central pulse wave velocity of a pregnant woman 101. The system comprises a first sound transducer 103, an optional second sound transducer 104, and a control unit 102.

In various embodiments, the system 100 may further comprise a display 105 and user input means 106. The display 106 may be any known display in the art such as an LCD, LED or OLED display. The user input means 106 may be any known user input means in the art such as a touch-interface, e.g. on the display 105, a keypad, a keyboard, a mouse or other pointer input means.

Each sound transducer 103, 104 is, during use, preferably releasably fastened to the patient 101 utilizing an adhesive, or an adhesive tape. The sound transducers 103, 104 may alternatively be known as microphones. As an alternative, the sound transducers may be accelerometers, which are able to convert vibrations caused by the sounds from maternal aortic valve opening and pulse wave arrival, respectively, to a recorded signal.

The first sound transducer 103 is adapted to measure the opening of the maternal aortic valve and the pulse wave arrival time at the uterine artery of the pregnant woman 101. The first sound transducer 103 is configured to send the recorded sound signal to the control unit 102

The optional second sound transducer 104 may be adapted to replace or augment the measurements of the first sound transducer 103. The second sound transducer 104 is configured to send the recorded sound signal to the control unit 102.

The first sound transducer 103 and the second sound transducer 104 are connected to the control unit 102 as indicated by the lines in FIG. 1. The line connecting the second sound transducer 104 and the control 102 is dashed to indicate that the second sound transducer 104 is optional. The connection is preferably wireless but may of course be wired. In FIG. 1 a parallel connection is shown, alternatively the first and second sound transducer 103, 104 may be connected in series to the control unit 102. Optionally, the first and second sound transducer 103, 104 may be connected in parallel to each other, whereby the recorded signal from each sound transducer is multiplexed on the connection to the control unit 102. The wireless connection may be a Bluetooth piconet or through another wireless protocol and standard such as WiFi.

The first and second sound transducers 103, 104 may be synchronized. Alternatively, the signals from the first and second sound transducers 103, 104 may be recorded simultaneously.

The control unit 102 comprises a processor and a non-transitory memory for storing instructions. The processor may be a general purpose processor or a processor specifically adapted to the functions of the present invention. The functionality of the present invention may be embodied wholly or partially in the control unit as various electronic modules, for example comprising AD converters as well as amplifiers and filters. Alternatively, the functionality of the present invention may be embodied wholly or partially in the control unit as various software modules. Hence, the skilled person realizes that the present invention is not limited to the restricted number of examples provided herein, but rather many different embodiments are to be construed encompassed by the present invention. For example, some of the functionality may be provided on an "on-demand" basis from a remote server, typically known as a "cloud-service".

In use, the first sound transducer 103 is arranged outside the body of the patient and releasably fastened preferably at the position of the anatomical projection of the uterine artery on the body of the pregnant woman 101 as shown in FIG. 1. It may be possible to arrange the first sound transducer 103 at other regions to detect the opening of the maternal aortic valve and the pulse wave arrival time at the uterine artery. For example, it may be sufficient to arrange the sound transducer within a 10 cm radius from the anatomical projection of the uterine artery.

The second sound transducer 104 may optionally be used to augment or replace the measured signal from the first sound transducer 103. This is due to the fact that some sounds may be stronger on one or the other side of the body of the patient. The second sound transducer 104 is, if used, arranged outside the body of the pregnant woman and releasably fastened contralateral on the abdomen to the first sound transducer 103 on the pregnant woman 101 as shown in FIG. 1. It may be possible to arrange the second sound transducer 104 at other regions to detect the opening of the maternal aortic valve and the pulse wave arrival time at the uterine artery.

The first and second sound transducers 103, 104 are thus understood to be placed in acoustic contact with the body of the patient 101 such that the sound transducers 103, 104 can record sounds or vibrations originating from within the body of the patient 101.

The control unit 102 is configured to receive measurement signals, also called recorded signals, from the first sound transducer 103 to identify the opening of the maternal aortic valve as a first time $t_a$, and to identify the pulse wave arrival time at the uterine artery as a second time $t_b$. The control unit 102 is further configured to determine the central transit time $T_c$ based on the difference between the second time $t_b$ and the first time $t_a$ and calculate the central pulse wave velocity cPWV based on an aortic length measurement $L_c$ and the central transit time $T_c$.

In order to calculate the central pulse wave velocity cPWV the control unit 102 may be configured to perform repeated measurements and calculations based on the recorded signals from one or more data points from the first and second sound transducers 103, 104. Thereby, an average central pulse wave velocity may be provided.

Figure 2:
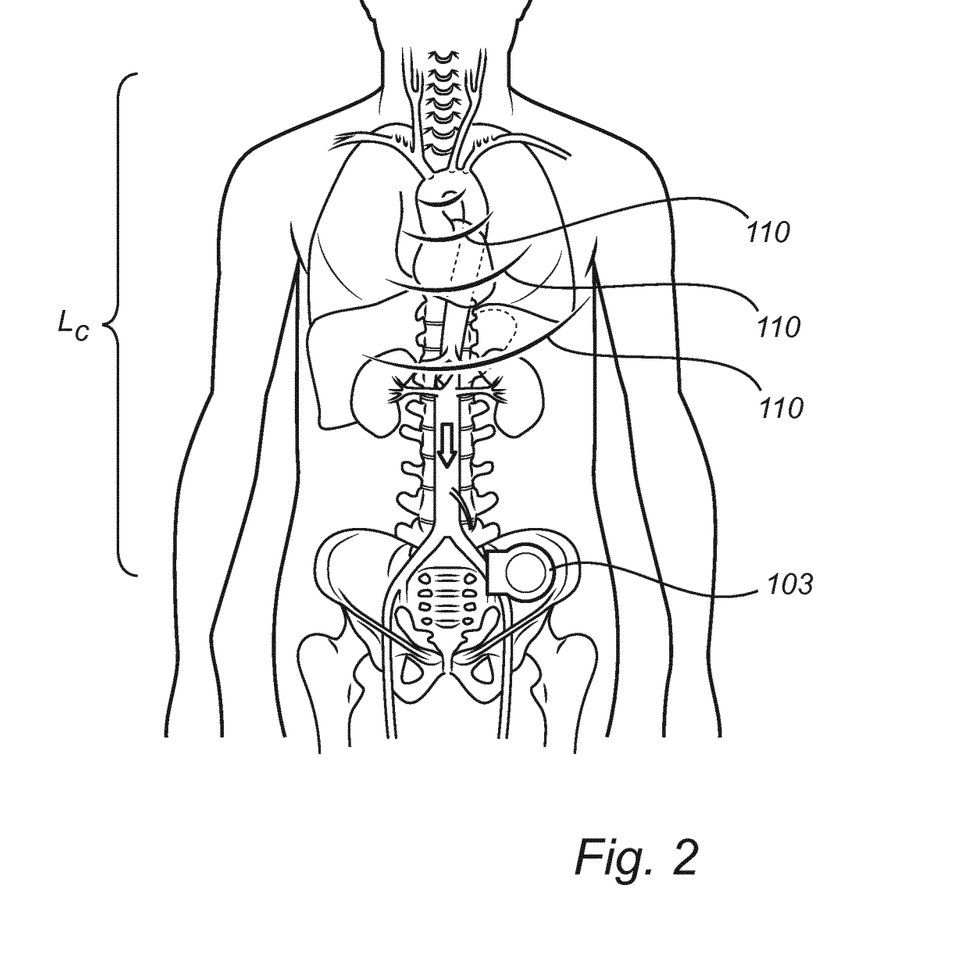
FIG. 2 is schematic view of a system according to at least one example embodiment of the invention.

In more detail, and with reference to FIG. 2 which shows a schematic cross-section of the pregnant woman 101, the central pulse wave velocity cPWV may be defined as the total aortic length $L_c$ divided by the central transit time $T_c$:

$$cPWV = \frac{L_c}{T_c}$$

The length of the human aorta may be approximated as the distance from the position of the hyoid bone to the position to the umbilicus. In the present invention, the length of the common and internal iliac arteries down to the uterine artery may also be needed to define the length of a human aortic path, as sound corresponding to a pulse wave reaching the uterine artery is obtained. Therefore, the total length travelled by blood flow from the aortic valve to the uterine artery may be provided as the length of a human aortic path $L_c$, e.g. measured or indicated as the position of the hyoid bone to the position of the anatomical projection of the uterine artery as shown in FIG. 2. It should be realized, however, that other measurements may be performed to approximate the length of travel of blood flow. For example, a measurement of the aortic length from the position of the hyoid bone to the position of the umbilicus may be used and multiplied with a factor for obtaining a measurement of the aortic length relevant to the travel of blood flow. Further, the patient records may contain prior measurements or approximations of the length of the aortic path made by MRI, X-ray or the like. The anatomical projection of the uterine artery should be understood as the anatomical projection on the front side of the body of the patient.

The central transit time $T_c$ is determined by the difference between the opening of the maternal aortic valve as a first time $t_a$ and the pulse wave arrival time at the aortic bifurcation as a second time $t_b$. The central transit time $T_a$ may thus be calculated as:

$$T_c = t_b - t_a$$

The opening of the maternal aortic valve, and the first time $t_a$, is preferably identified by the S1-heart sound. The S1-heart sound typically comprises sound in the frequencies of 25 Hz to 200 Hz. The opening of the maternal aortic valve, and thus the first time $t_a$ may be identified by sounds having a frequency in the range of 1 Hz to 200 Hz. However, using a smaller frequency range, such as 25 Hz to 200 Hz may facilitate the identification of the low frequency heart sound.

The opening of the maternal aortic valve is detected via the sound waves 110 travelling within the body of the pregnant woman 101. These sound waves 110 may travel along the body of the pregnant woman 110 as the fluid-filled enlarged uterus conducts the maternal heart sound to the abdomen. This enables the single sound transducer, i.e. sound transducer 103, to measure the opening of the maternal aortic valve and also the arrival of the pulse wave in the uterine artery.

The pulse wave arrival time at the uterine artery, and thus the second time $t_b$, is identified by sounds having a frequency range of 200 Hz to 800 Hz. Hence, the frequency components of the pulse wave may also be used to identify the pulse wave. For example, a frequency filter may be used in the sound transducer 103, or in the control unit 102. Alternatively, the control unit 102 may use a frequency separation, in software or hardware, to distinguish the pulse wave.

The central transit time $T_c$ may also be modified by the use of a constant $t_{ict}$. The constant $t_{ict}$ represents the average cardiac iso-volumetric contraction time, which is the time from the beginning of the maternal ventricular contraction (signified by the start of the first heart sound) to the opening of the maternal aortic valve. Typically, $T_{ict}$ is in the range of 30 ms to 40 ms. The use of the constant $T_{ict}$ may thus offset the contraction time of the heart such that the accuracy of the central transit time is improved:

$$T_c = t_b - t_a - t_{ict}$$

There are of course several different variations and embodiments possible of the technology described in the foregoing; the control unit 102 may be configured to automatically identify the first time $t_a$ and second time $t_b$ from the recorded signals from the first sound transducer 103 and then provide the central pulse wave velocity cPWV. Alternatively, the control unit 102 may be further configured to display the measurements from the first sound transducer 103 on a display 105 with the determined first time $t_a$ and second time $t_b$, respectively. Then user input may be received via user input means 106 to identify the first time and the second time; whereby the first and second time may be corrected based on the user input. The corrected first and second time are used for determining the central transit time $T_c$ and calculating the central pulse wave velocity cPWV by the control unit 102.

To automatically identify the first and second time from the recorded signals, the control unit 102 may comprise a database which comprises a large number of validation measurements of the sounds signals in healthy subjects. Then, the processor of the control unit 102 may use curve fitting, least squares approximation or machine learning to identify the opening of the maternal aortic valve and the pulse wave arrival time at the uterine artery as measurement signals from the first sound transducer which are similar and comparable to the measurement from healthy subjects. As an alternative, an algorithm for processing the received signal may be used, wherein the algorithm is adapted to detect and identify the points in time.

In another embodiment, the control unit 102 may be configured to display the recorded signals from the first sound transducer 103 on a display 105. The control unit 102 is further configured to receive user input via the user input means 106 to identify the opening of the maternal aortic valve and the pulse wave arrival time at the uterine artery, and to receive an aortic length measurement $L_c$ via the user input means. The control unit 102 then determines the central transit time $T_c$ based on the difference between the second time and the first time and calculates the central pulse wave velocity based on an aortic length measurement and the central transit time as described in the foregoing.

It should of course be noted that the control unit 102 may be configured to calculate an average central pulse wave velocity from a plurality of measurements by the first sound transducer 103. The reliability and robustness of the calculated average central pulse wave velocity may thus be improved.

Further, the second sound transducer 104 mentioned in the foregoing may be utilized to augment or replaced the recorded signals from the first sound transducer 103. Hence, the control unit 102 may be configured to determine which sound transducer that acquires the strongest signals and use the recorded signal from the sound transducer providing the best signals. Strongest signal may refer to at least one of highest amplitude, facilitation of the detection of the opening of the maternal aortic valve, facilitation of the detection of the pulse wave arrival time at the uterine artery.

For instance, if the placenta of the pregnant woman is left-sided, blood flow in the right side uterine artery may be reduced, due to a drop of resistance in the ipsilateral artery and a rise of resistance in the contralateral artery. Depending on the placement of the placenta, the measurements by one of the first sound transducer 103 and second sound transducer 104 may be of higher relevance and the control unit 102 may be configured to process only the signal of interest. However, it may also be relevant to form a mean cPWV based on the signals from both the first sound transducer 103 and the second sound transducer 104. The mean cPWV may be particularly relevant when the placenta is centrally positioned and there is a similar blood flows on both the left and right side uterine arteries.

Figure 3:
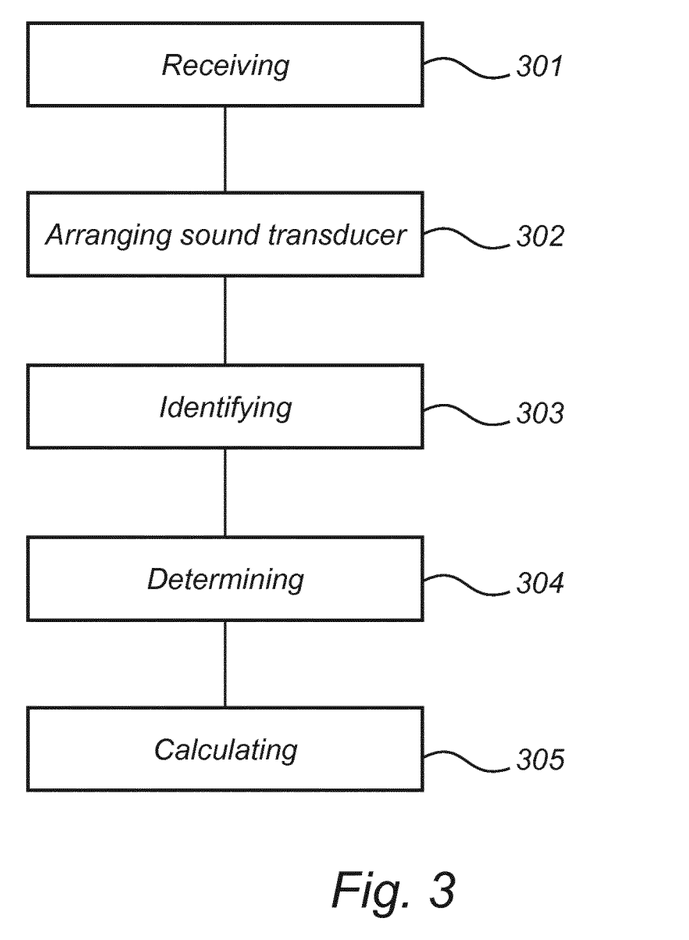
FIG. 3 is a flowchart schematically illustrating at least one example embodiment of the invention.

FIG. 3 is a flowchart schematically illustrating a method for determining central pulse wave velocity according to at least one embodiment of the invention. It is noted that these method steps correspond to the functions of the system 100 described in the foregoing, however, the method may of course also be performed with another system.

The first step 301 comprises receiving an indication of a measurement of a length of a human aortic path to provide an aortic length $L_c$.

The next step 302 comprises arranging a sound transducer 103 on the patient 101. The first sound transducer 103 is preferably releasably fastened at the position of the anatomical projection of the uterine artery on the body of the pregnant woman 101 as shown in FIG. 1.

The sound transducer 103 may alternatively be arranged at other regions of the body of the pregnant woman 101 in question to record the opening of the maternal aortic valve and the pulse wave arrival time at the uterine artery.

It should be noted that the steps 301 and 302 may be performed in any order as they are not dependent upon each other.

The next step 303 comprises identifying the opening of the maternal aortic valve with measurement from the sound transducer 103 as a first time $t_a$, and the pulse wave arrival time at the uterine artery with measurements from the sound transducer 103 as a second time $t_b$.

The step 303 may be performed either automatically by a control unit 102 and processor or be corrected and verified by user input, or the identification may be performed manually by user input. These alternative embodiments are outlined above in connection with FIG. 1.

The next step 304 comprises determining the central transit time $T_c$ based on the difference between the second time $t_b$ and the first time $t_a$. The first time $t_a$ is subtracted from the second time $t_b$ to provide the central transit time $T_c$. Alternatively, a constant $t_{ict}$ may also be subtracted from the second time $t_b$ to increase the accuracy of the central transit time $T_c$ as outlined above.

The next step 305 comprises calculating the central pulse wave velocity cPWV based on the aortic length $L_c$ and the central transit time $T_c$. The central pulse wave velocity cPWV is preferably calculated as the total aortic length $L_c$ divided by the central transit time $T_c$ acquired in the previous step 304.

The method may be repeated to provide an average central pulse wave velocity from a plurality of measurements from the sound transducer(s). The reliability and robustness of the calculated average central pulse wave velocity may thus be improved.

Variations and alternative embodiments of the method outlined above and in connection with FIG. 3 should be understood to correspond to the embodiments elucidated in connection with the system 100 explained in conjunction with FIGS. 1 and 2.

Figure 4:
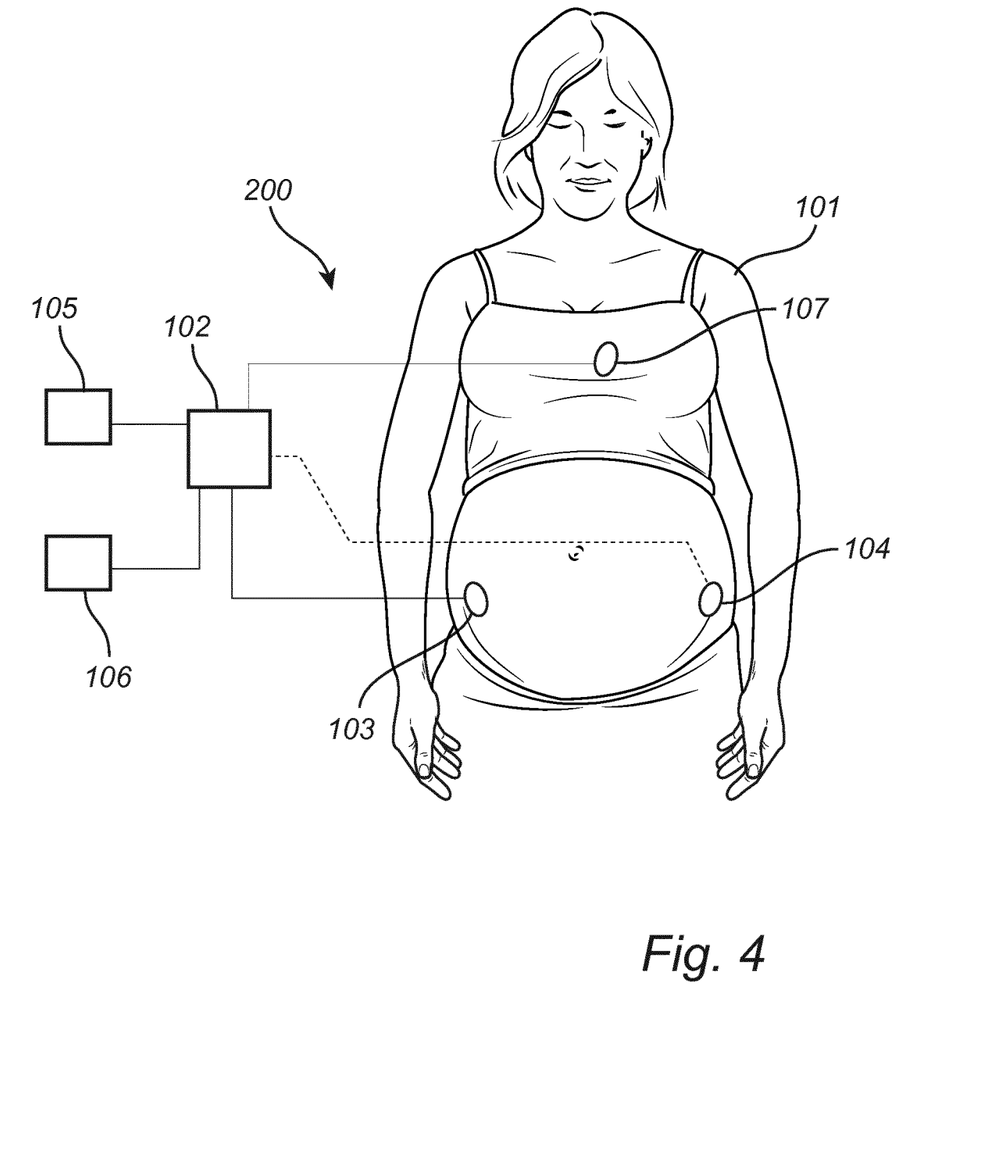
FIG. 4 is schematic view of a system according to at least one example embodiment of the invention.

FIG. 4 is a schematic view of a system 200 for determining the central pulse wave velocity of a pregnant woman 101. The system 200 comprises the same or similar components as the system 100 described in the foregoing. Reference characters in FIG. 4 being the same as the reference characters in FIG. 1 refer to the same elements.

A difference between the system 100 and the system 200 shown in FIG. 4 is that the system 200 further comprises a third sound transducer 107, although there may only be two sound transducers if the optional second sound transducer 103 is not used.

The third sound transducer 107 is preferably arranged, during use, at the aortic valve auscultation region of the patient 101 for measuring the maternal aortic valve opening time. The aortic auscultation region is located between the second and third rib on a human patient. Hence, there is some leeway and freedom in the exact placement of the third sound transducer 107.

Similar to the first and second sound transducers 103, 104 the third sound transducer 107 is, during use, preferably releasably fastened to the patient 101 utilizing an adhesive, or an adhesive tape. The third sound transducer 107 may alternatively be known as a microphone. As an alternative, the third sound transducer 107 may be an accelerometer, which is able to convert vibrations caused by the sounds from maternal aortic valve opening to a recorded signal.

The first sound transducer 103 is adapted to measure the opening of the maternal aortic valve of the pregnant woman 101. The third sound transducer 107 is configured to send the recorded sound signal to the control unit 102.

The third sound transducer 107 may be adapted to replace or augment the measurements of the first sound transducer 103 and/or the optional second sound transducer 104 with regarding to the identification of the opening of the maternal aortic valve.

The third sound transducer 107 is connected to the control unit 102 as indicated by the lines in FIG. 4. The connection is preferably wireless but may of course be wired. In FIG. 4 a parallel connection is shown, alternatively the first, second and third sound transducers 103, 104, 107 may be connected in series to the control unit 102. Optionally, the first, second and third sound transducer 103, 104, 104 may be connected in parallel to each other, whereby the recorded signal from each sound transducer is multiplexed on the connection to the control unit 102. The wireless connection may be a Bluetooth piconet or through another wireless protocol and standard such as WiFi.

The third sound transducer 107 may be adapted to measure the opening of the aortic valve of the patient 101. To this end, in various exemplary embodiments, the opening of the maternal aortic valve, and the first time $t_a$, is preferably identified by a low frequency heart sound which occurs simultaneously as the S1-heart sound. The low frequency heart sound comprises sound waves in the frequency range of 1 Hz to 25 Hz. The third sound transducer 107 may comprise a low pass filter having a cutoff frequency of 300 Hz, or a band pass filter having a lower cutoff frequency at 25 Hz and a higher cutoff frequency at 200 Hz. In another exemplary embodiment, the third sound transducer 107 comprises a low pass filter having a cutoff frequency of 25 Hz. In yet another exemplary embodiment, the third sound transducer may comprise a first bandpass filter recording sound waves in the frequency range of 1 Hz to 25 Hz and a second bandpass filter recording sound waves in the frequency range of 25 Hz to 300 Hz. Alternatively, a low pass filter or band pass filter with the above noted cutoff frequencies may be arranged in the control unit 102 which receives the recorded signals from the third sound transducer 107.

In use, the first sound transducer 103 is arranged outside the body of the patient and releasably fastened preferably at the position of the anatomical projection of the uterine artery on the body of the pregnant woman 101. It may be possible to arrange the first sound transducer 103 at other regions to detect the opening of the maternal aortic valve and the pulse wave arrival time at the uterine artery.

The second sound transducer 104 may optionally be used to augment or replace the measured signal from the first sound transducer 103. This is due to the fact that some sounds may be stronger on one or the other side of the body of the patient. The second sound transducer 104 is, if used, arranged outside the body of the pregnant woman and releasably fastened contralateral on the abdomen to the first sound transducer 103 on the pregnant woman 101 as shown in FIG. 1. It may be possible to arrange the second sound transducer 104 at other regions to detect the opening of the maternal aortic valve and the pulse wave arrival time at the uterine artery.

The first, second and third sound transducers 103, 104, 107 are thus understood to be placed in acoustic contact with the body of the patient 101 such that the sound transducers 103, 104 can record sounds or vibrations originating from within the body of the patient 101.

The first, second and third sound transducers 103, 104, 107 may be synchronized. Alternatively, the signals from the first, second and third sound transducers 103, 104, 107 may be recorded simultaneously by the control unit 102. Thereby, the central transit time may be calculated as the difference between the first and second time. The first, second and third sound transducers 103, 104, 107 may be synchronized by any known means, for example the measurement from the first, second and third sound transducers 103, 104, 107 may be time-stamped. Alternatively, the control unit 102 may synchronize the received measurement signals.

The control unit 102 is configured to receive measurement signals, also called recorded signals, from the third sound transducer 103 to identify the opening of the maternal aortic valve as a first time $t_a$, and to receive measurement signals, also called recorded signals, from the first sound transducer 103 (and/or the optional second sound transducer 104) to identify the pulse wave arrival time at the uterine artery as a second time $t_b$. The control unit 102 is further configured to determine the central transit time $T_c$ based on the difference between the second time $t_b$ and the first time $t_a$ and calculate the central pulse wave velocity cPWV based on an aortic length measurement $L_c$ and the central transit time $T_c$. The details and variations of this detection, i.e. automatic, user input correction, or user input to identify the first and second time are described in the foregoing and are left of for sake of brevity. However, those variations are of course also possible to use for the system 200 with the third sound transducer 107.

In order to calculate the central pulse wave velocity cPWV the control unit 102 may be configured to perform repeated measurements and calculations based on the recorded signals from one or more data points from the first, second and third sound transducers 103, 104, 107. Thereby, an average central pulse wave velocity may be provided.

The skilled person also realizes that there are further variations and embodiments which are possible and within the scope of the invention. For example, more than two sound transducers may be used to enhance or replace the detection of the opening of the maternal aortic valve and the pulse wave arrival time at the uterine artery. Further, the identification of the opening of the maternal aortic valve and the pulse wave arrival time at the uterine artery may be wholly or partially automatic by algorithms or curve fittings as described in the foregoing. Furthermore, the detection may be enhanced by restricting which frequencies are comprised in the recorded signals, either by electrical filters comprised in the sound transducers or the control unit, or by software filters comprised in the control unit.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Additionally, even though the invention has been described with reference to specific exemplifying embodiments thereof, many different alterations, modifications and the like will become apparent for those skilled in the art. Variations to the disclosed embodiments can be understood and effected by the skilled person in practicing the claimed invention, from a study of the drawings, the disclosure, and the appended claims. Furthermore, in the claims, the word "comprising" does not exclude other elements or steps, and the indefinite article "a" or "an" does not exclude a plurality.

The embodiments of the present disclosure may be implemented using existing computer processors, or by a special purpose computer processor for an appropriate system, incorporated for this or another purpose, or by a hardwired system.

The invention claimed is:

1. A method for determining a central pulse wave velocity in a pregnant woman, the method comprising:
   receiving an indication of a measurement of a length of a human aortic path outside the body to provide an aortic length;
   arranging a sound transducer, outside the body of the patient, at the position of the anatomical projection of the uterine artery;
   identifying the opening of the maternal aortic valve with measurement from the sound transducer as a first time, and the pulse wave arrival time at the uterine artery with measurements from the sound transducer as a second time;
   determining the central transit time based on the difference between the second time and the first time; and
   calculating the central pulse wave velocity based on the length of the human aortic path and the central transit time.

2. The method according to claim 1, wherein the opening of the maternal aortic valve is identified by sounds having a frequency range below 100 Hz.

3. The method according to claim 1, wherein the pulse wave arrival time at the uterine artery is identified by sounds having a frequency range of 200 Hz to 800 Hz.

4. The method according to claim 1, wherein the sound transducer is a first sound transducer and the method further comprises:
   arranging a second sound transducer, outside the body of the patient, contralateral on the abdomen to the position of the first sound transducer.

5. The method according to claim 1, wherein identifying the opening of the maternal aortic valve with measurement from the sound transducer as a first time, and the pulse wave arrival time at the uterine artery with measurements from the sound transducer as a second time is performed automatically by a control unit comprising a processor.

6. The method according to claim 5, wherein the method further comprises:
   displaying the measurements from the sound transducer on a display;

receiving user input to identify the first time and the second time; and correcting the first time and the second time based on the user input, wherein the corrected first and second time are used for determining the central transit time and calculating the central pulse wave velocity.

7. The method according to claim 1, wherein identifying the opening of the maternal aortic valve with measurement from the sound transducer as a first time, and the pulse wave arrival time at the uterine artery with measurements from the sound transducer as a second time further comprises:

displaying the measurements from the sound transducer on a display;

receiving user input to identify the first time and the second time.

8. The method according to claim 1, wherein the method is repeated to provide an average central pulse wave velocity from a plurality of measurements by the sound transducer.

9. A system for determining a central pulse wave velocity in a pregnant woman, the system comprising:

a sound transducer adapted to measure the opening of the maternal aortic valve and the pulse wave arrival time at the uterine artery with measurements;

a control unit connected to the sound transducer; and wherein the control unit is configured to receive measurement signals from the sound transducer to identify the opening of the maternal aortic valve as a first time, and to receive measurements signals from the sound transducer to identify the pulse wave arrival time at the uterine artery as a second time, and wherein the control unit is further configured to determine the central transit time based on the difference between the second time and the first time and calculate the central pulse wave velocity based on an aortic path length measurement and the central transit time.

10. The system according to claim 9, wherein the opening of the maternal aortic valve is identified by sounds having a frequency range below 100 Hz.

11. The system according to claim 9, wherein the pulse wave arrival time at the uterine artery is identified by sounds having a frequency range of 200 Hz to 800 Hz.

12. The system according to claim 9, further comprising a display and user input means.

13. The system according to claim 12, wherein the control unit is configured to display the measurements from the sound transducer on the display, and to receive user input to identify the first time and the second time, wherein the control unit is configured to correct the first time and the second time based on the user input, wherein the corrected first and second time are used to determine the central transit time and calculate the central pulse wave velocity.

14. The system according to claim 9, wherein the sound transducer is a first sound transducer and the system further comprises a second sound transducer adapted to measure the opening of the maternal aortic valve and the pulse wave arrival time at the uterine artery with measurements, wherein the second sound transducer is adapted to be placed contralateral on the abdomen to the position of the first sound transducer and augment or replace the measurements of the first sound transducer.

15. The system according to claim 9, wherein the sound transducer is a first sound transducer and the system further comprises a third sound transducer adapted to measure the opening of the maternal aortic valve, wherein the third sound transducer is adapted to be placed at the aortic valve auscultation region of the patient for measuring the maternal aortic valve opening time and replace the measurements of the first sound transducer with respect to identifying the maternal valve opening time.

16. A system for determining a central pulse wave velocity in a pregnant woman, the system comprising:

a sound transducer adapted to measure the opening of the maternal aortic valve and the pulse wave arrival time at the uterine artery;

a display;

user input means;

a control unit connected to the sound transducer, the display and the user input means; and wherein the control unit is configured to receive measurement signals from the sound transducer, and display the measurements on the display, and to receive user input via the user input means to identify the opening of the maternal aortic valve as a first time and the pulse wave arrival time at the uterine artery as a second time, and to receive an aortic length measurement, wherein the control unit is further configured to determine the central transit time based on the difference between the second time and the first time and calculate the central pulse wave velocity based on an aortic length measurement and the central transit time.

* * * * *